(12) United States Patent
Dragan et al.

(10) Patent No.: US 6,593,498 B2
(45) Date of Patent: Jul. 15, 2003

(54) METHOD FOR PREPARATION OF BORATABENZENE DERIVATIVES

(75) Inventors: Vladimir Dragan, Chester, NY (US); Ramesh Krishnamurti, Bangalore (IN)

(73) Assignee: Equistar Chemicals, L.P., Houston, TX (US)

( * ) Notice: Subject to any disclaimer, the term of this patent is extended or adjusted under 35 U.S.C. 154(b) by 0 days.

(21) Appl. No.: 09/925,048

(22) Filed: Aug. 8, 2001

(65) Prior Publication Data

US 2003/0055289 A1 Mar. 20, 2003

(51) Int. Cl.$^7$ .................................................. C07F 5/02
(52) U.S. Cl. ............................................................ 568/1
(58) Field of Search ......................................... 568/1, 6

(56) References Cited

U.S. PATENT DOCUMENTS 6,150,560 A * 11/2000 Lee et al. ...................... 568/6

OTHER PUBLICATIONS

Organometallics by Hoic et al vol. 15 pp. 1315–1318 1996.*
CA:91:174738 abs of Synthesis by Verkruijsse et al (4) pp 292–3 1979.*
CA:90:187062 abs of J Org Chem by Ashe 44(9) pp 1409–13 1979.*
"Simply Substitute Boraethenes", Angew. Chem. Int. Ed. Engl. 24 (1985) No. 12, pp. 1065–1066.
"Regiochemical Control in the Hydrostannylation of Aryl Substitute Alkynes: a Stereoselective Synthesis of Disubstituted Vinylstannanes," Synlett 1999, pp. 246–248.
"An Improved Synthesis of 1,4–Diynes," 1979 Georg Thieme Publishers, pp. 292–293.
"A New Approach for the Generation and Reaction of Organotin Hydrides: The Development of Reactions Catalytic in Tin," J. Org. Chem. 1999, 64, pp. 342–343.
"Unique Property of Copper(I) Chloride as a Radical Initiator as well as a Lewis Acid: Application to CuCl– Catalyzed Aldol Reaction α, β–Unsaturated Ketones with $Bu_3SnH$," Tetrahedron Letters 40 (1999) pp. 2133–2136.
"3–Phenyl–3–Benzoborepin, A Carbon–Boron Heterocycle with Aromatic Character," Tetrahearon Letters No. 14, pp. 1263–1266, 1967.
"Application of Fluoride–Catalyzed Silane Reductions of Tin Halides to the in Situ Preparation of Vinylstannanes," J. Org. Chem. (1999), 64, pp. 5958–5965.
"The Synthesis and Some Reactions of a Series of "Skipped" Polyacetylenes Containing Terminal Acetylene Groups*," Tetrahedron. vol. 25, pp. 2823–2835 (1969).
"The 1–Phenylborabenzene Anion," Journal of American Chemical Society, 1971, pp. 1804–1805.
"Bis (1–substituted–borabenzene) iron Complexes," Journal Of American Chemical Society, 1975 (2 pgs.).
"Boratastilbene Synthesis, Structural Characterization, and Photophysics," J. Am. Chem. Soc. 2000, pp. 3969–3970.

* cited by examiner

*Primary Examiner*—Jean F. Vollano
(74) *Attorney, Agent, or Firm*—Brooks & Kushman P.C.

(57) ABSTRACT

The present invention provided an improved method for preparing a boratabenzene derivative. The invention includes an improved preparation of 1,4-pentadiyne, 1-haloboracyclohexa-2,5-diene, and 1-methylboracyclohexa-2,5-diene intermediates. These compounds are chemically labile and are not directly isolated from solution. Furthermore, the invention discloses an improved preparation of 1,1-dialkylstannacyclohexa-2,5-diene, another intermediate useful for preparing boratabenzene derivatives.

21 Claims, No Drawings

METHOD FOR PREPARATION OF BORATABENZENE DERIVATIVES

BACKGROUND OF THE INVENTION

1. Field of the Invention

This invention relates to a method of preparing a boratabenzene-containing metal complex.

2. Background Art

The usefulness of olefin polymerization catalysts containing a transition metal pi-bonded to a ligand that contains a boratabenzene ring has recently been realized. Such catalysts may be used in the homo- and co-polymerization of ethylene and other olefinic hydrocarbons. These catalysts offer several advantages over the conventional Ziegler catalyst systems which contain a transition metal and one or more organometallic compounds. Specifically, the boratabenzene-containing catalysts have exhibited higher activities, thereby making it feasible to use a lesser amount of the catalyst. Lower concentrations of the boratabenzene catalysts have made it less important to remove catalyst residues. Conventional catalysts have required that neutralizing agents and stabilizers be added to the polymers to overcome the deleterious effects of the catalyst residues. Failure to remove residues results in polymers having a yellow or grey color and poor ultraviolet and long term stability. Chloride-containing Ziegler catalysts can cause corrosion in polymer processing equipment. Ziegler catalysts tend to produce polymers with a broad molecular weight distribution, which is less desirable for injection molding applications. Furthermore, Ziegler catalysts are not very efficient at incorporating α-olefin co-monomers, thereby making it difficult to control polymer density.

Although Ziegler catalysts have been improved, these catalysts are being replaced with metallocene catalyst systems. A metallocene consists of a transition metal with two or more cyclopentadienyl ligands attached. The metallocene catalysts have low activities when used with organometallic co-catalysts such as aluminum alkyls, but have high activities when used with aluminoxanes as co-catalysts. Activities are so high that it is not necessary to remove the catalyst residue from the polymer. These catalysts also incorporate α-olefins well. However, at high temperature they tend to produce lower molecular weight polymers. As such, they are most useful for gas phase and slurry polymerizations of ethylene which are typically conducted between 80 and 95° C. The improved co-polymerization of ethylene is desirable because it allows greater flexibility for producing polymers over a wider range of densities as well.

Relatively few synthetic routes to boratabenzene-containing compounds are known. An early route was the hydrostannylation of 1,4-pentadiyne with dibutylstannane to give boracyclohexadiene on exchange with boron halides. Boracyclohexadiene is then deprotonated with a base such as lithium diisopropylamide (LDA) to give lithium boratabenzene. However, 1,4-pentadiyne tends to be unstable and somewhat difficult to prepare in high yields. Another route for preparing boratabenzene is based on the metalation induced ring closure of [bis(dialkylamino)boryl] pentadienes. Improved methods of preparing boratabenzene-containing compounds in high yield and high volume are needed.

SUMMARY OF THE INVENTION

The present invention provides a method for preparing a boratabenzene derivative or a boratabenzene-containing complex. Boratabenzene has the following formula:

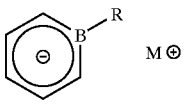

(I)

where R is hydrogen, a $C_{1-8}$ alkyl group, $C_{6-10}$ aryl group, $C_{7-15}$ aralkyl group, $C_{1-10}$ alkoxy group, $C_{6-14}$ aryloxy group, $C_{1-8}$ dialkylamino group, or $C_{6-15}$ diarylamino group.

In one embodiment of the present invention an improved method for forming a 1,4-pentadiyne is provided. The 1,4-pentadiyne is formed by reacting an alkynyl magnesium bromide with an alkynyl benzenesulfonate in a first solvent. A second solvent is added to the reaction vessel to form a second solution. The second solution is distilled and a third solution comprising the second solvent and the 1,4-pentadiyne is collected. This second solvent is suitable for the next step in the preparation of the boratabenzene derivative. In this preparation, the 1,4-pentadiyne is not directly separated from at least one solvent. This is advantageous because 1,4-pentadiyne compounds are unstable and reactive. The 1,4-pentadiyne is reacted with a dialkytin dihydride to form a 1,1-dialkylstannacyclohexa-2,5-diene.

In another embodiment of the present invention, the 1,1-dialkylstannacyclohexa-2,5-diene is reacted with a boron trihalide and then an alkylating agent to form a 1-alkylboracyclohexa-2,5-diene. The 1-alkylboracyclohexa-2,5-diene is converted into a boratabenzene by reaction with a strong base. In another embodiment of the present invention, the 1,1-dialkylstannacyclohexa-2,5-diene is reacted with a alkylboron dihalide or an arylboron dihalide to form the corresponding 1-alkyl- or 1-arylboracyclohexa-2,5-diene. The 1-alkylboracyclohexa-2,5-diene is reacted with a strong base to form a 1-alkylboratabenzene derivative.

In still another embodiment of the invention, a 1,1-diakylstannacyclohexa-2,5-diene suitable for preparing a boratabenzene-containing complex is provided. This embodiment is suitable for any preparation of a boratabenzene derivative that utilizes a 1,1-diakylstannacyclohexa-2,5-diene derivative. Polymethyihydrosiloxane, potassium fluoride, a catalytic amount of 2,2-azobisisobutyronitrile, a 1,4-pentadiyne derivative, and a dialkytin dihalide are reacted together. This reaction produces a 1,1-dialkylstannacyclohexa-2,5-diene in high yields. A 1-alkylboratabenzene and a boratabenzene-containing complex are formed as described above.

In yet another embodiment of the present invention, an improved method for preparing a 1-chloroboracyclohexa-2,5-diene is provided. In this embodiment, 1,1-dibutylstannacyclohexa-2,5-diene is reacted with a boron trihalide in a first solvent to form the 1-chloroboracyclohexa-2,5-diene. A second less volatile solution is then added and the first solvent is removed under vacuum. This second solvent is suitable for the next step in the preparation of the boratabenzene derivative as described above.

DETAILED DESCRIPTION OF THE PREFERRED EMBODIMENT(S)

Reference will now be made in detail to presently preferred embodiments and methods of the invention, which constitute the best modes of practicing the invention known to the inventors.

In accordance with one embodiment of the invention, a presently preferred method of preparing a boratabenzene complex is provided. The method of the present invention comprises the preparation of a 1,4-pentadiyne derivative. The 1,4-pentadiyne derivative is prepared by forming a first reaction solution comprising an alkynyl magnesium bromide with an alkyipropargyl benzenesulfonate and a catalytic amount of copper (I) bromide in an inert solvent. The preferred alkynyl magnesium bromide has the formula:

$$BrMg\!-\!\!\equiv\!\!-\!R_1 \tag{II}$$

where $R_1$ is hydrogen, a $C_{1-10}$ alkyl group, a $C_{6-10}$ aryl group, or a $C_{7-15}$ aralkyl group. The preferred alkynyl magnesium bromide is ethynyl magnesium bromide. The alkylpropargyl benzenesulfonate has the formula:

(III)

where $R_2$ is hydrogen, a $C_{1-10}$ alkyl group, a $C_{6-10}$ aryl group, or a $C_{7-15}$ aralkyl group. The alkynyl magnesium bromide is preferably made by anion exchange by reacting an alkynyl magnesium chloride with a bromide salt such as lithium bromide. The preferred inert solvent for performing the reaction will typically be an ether. The preferred solvent is di(ethylene glycol) dibutyl ether. After the reaction is complete, a second solvent is added to form a second reaction solution. The second solvent must be chemically unreactive with regards to the 1,4-pentadiyne derivative which is formed during the reaction. Furthermore, this second solvent is more volatile than the first solvent. Preferred second solvents are toluene and benzene. This second solution is then distilled and a third solution comprising the 1,4-pentadiyne derivative and the second solvent is collected. This second solvent is suitable for the next step in the preparation of the boratabenzene derivative. The structure of the 1,4-pentadiyne derivative is:

(IV)

The third solution is reacted with a dialkyl tin dihydride having the formula:

(V)

where $R_3$ is a $C_{1-10}$ alkyl group, a $C_{6-10}$ aryl group, or a $C_{7-15}$ aralkyl group or a $C_{1-10}$ alkyl group and $R_4$ is a $C_{1-10}$ alkyl group, a $C_{6-10}$ aryl group, or a $C_{7-15}$ aralkyl group. The resulting product of this reaction is a 1,1-dialkylstannacyclohexa-2,5-diene having the formula:

(VI)

This 1,1-dialkylstannacyclohexa-2,5-diene is then reacted with a boron halide with the formula:

$$BX_3 \tag{VII}$$

where X is a halogen to form a 1-haloboracyclohexa-2,5-diene having the formula:

(VIII)

In a particularly preferred embodiment, the preferred boron halide is boron trichloride.

The 1-haloboracyclohexa-2,5-diene derivative is next reacted with an alkylating agent to form a 1-alkylboracyclohexa-2,5-diene derivative having the formula:

(IX)

where $R_5$ is a $C_{1-10}$ alkyl group, a $C_{6-10}$ aryl group, or a $C_{7-15}$ aralkyl group. The preferred alkylating agents are trialkylaluminum and dialkylzinc compounds. The preferred alkylating agents are trimethylaluminum, triethylaluminum, dimethylzinc, and diethylzinc.

The 1-alkylboracyclohexa-2,5-diene derivative is next reacted with a strong base to form a 1-alkylboratabenzene having the formula:

(X)

Finally, the 1-alkylboratabenzene is converted to a boratabenzene-containing metal complex by reacting the 1-alkylboratabenzene with a transition or lanthanide metal complex. Preferred transition or lanthanide metal complexes include $CpZrCl_3$ (Cp=cyclopentadienyl group).

In another embodiment of the present invention, the boron halide that is reacted with the 1,1-dialkylstannacyclohexa-2,5-diene derivative described by structure VI has the formula:

$$R_5BX_2 \tag{XI}$$

where $R_5$ is a $C_{1-10}$ alkyl group, a $C_{6-10}$ aryl group, or a $C_{7-15}$ aralkyl group and X is a halogen. The resulting product of this reaction is 1-alkyl boracyclohexa-2,5-diene given by formula IX. The 1-alkylboracyclohexa-2,5-diene derivative is next reacted with a strong base to form the 1-alkylboratabenzene given by formula X.

Finally, the 1-alkylboratabenzene is converted to a boratabenzene-containing complex by reacting the 1-alkylboratabenzene having with a transition or lanthanide metal complex. Preferred transition or lanthanide metal complexes include $CpZrCl_3$ (Cp=cyclopentadienyl group).

In another embodiment of the invention, a 1,1-diakylstannacyclohexa-2,5-diene suitable for preparing a boratabenzene-containing complex is provided. The 1,1-diakylstannacyclohexa-2,5-diene is used to prepare the boratabenzene-containing complex as described above. Alternatively, this embodiment is suitable for any preparation of a boratabenzene-containing complex that utilizes a 1,1-diakylstannacyclohexa-2,5-diene derivative. In this embodiment, polymethyihydrosiloxane, potassium fluoride, a catalytic amount of 2,2-azobisisobutyronitrile, the 1,4-pentadiyne derivative with structure IV, and a dialkytin dichloride are reacted together. The dialkyltin dichloride has the following structure:

XII

This reaction produces the 1,1-dialkylstannacyclohexa-2,5-diene described by structure VI in high yields. A 1-alkylboratabenzene and a boratabenzene-containing complex are formed as described above.

In another embodiment of the invention, an improved method for preparing a 1-haloboracyclohexadiene such as 1-chioroboracyclohexadiene suitable for preparing a boratabenzene-containing complex is provided. In this embodiment, 1,1-dibutylstannacyclohexa-2,5-diene is reacted with a boron trihalide such as boron trichloride in a first solvent. Upon completion of the reaction a second solvent is added to the reaction mixture. Both the first solvent and the second solvent must be chemically unreactive towards the reactants and products formed from this reaction. Furthermore, the first solvent has a greater volatility than the second solvent and the second solvent must be a suitable solvent for the next step in the preparation of the boratabenzene derivative. Preferred first solvents include methylene chloride and chloroform, and preferred second solvents include low chain hydrocarbons such as heptane, octane, nonane, decane, and mixtures thereof. Next, the first more volatile solvent is removed at a reduced pressure to form a solution comprising the reaction product, a 1-haloboracyclohexadiene such as 1-chloroboracyclohexadiene and the second solvent. In the next step, this solution is distilled yielding a second solution comprising 1-chloroboracyclohexadiene and the solvent. This second solution may be used directly without further isolation of the 1-haloboracyclohexadiene to produce the 1-alkylboratabenzene derivative and a boratabenzene-containing complex as described above. This embodiment is particularly useful in preparing 1-chloroboracyclohexadiene which is relatively unstable and difficult to isolate, being at the same time a key intermediate in boratabenzene derivatives synthesis.

EXAMPLE 1

Preparation of 1,4-Pentadiyne

A 22 l flask equipped with a mechanical stirrer, thermowell, liquid inlet tube connected to a metering pump and a condenser is assembled. Vacuum is applied to the system followed by the addition of dry nitrogen. The vacuum—nitrogen procedure is repeated three times. This is done to ensure that moisture and oxygen are excluded from the reaction assembly. A nitrogen pad is maintained in the reactor.

Ethynylmagnesium chloride in di(ethylene glycol) dibutyl ether (8.34 kg, 10.50 moles, 1.18 Molar, density=0.937 g/ml) is charged to the reactor. Oven dried lithium bromide (934.84 g, 10.77 moles) is added to the reactor and the mixture is stirred for one hour at 20 to 30° C. Copper (I) Bromide (42.4 g, 0.3 moles) is then added to the reactor and the mixture is stirred for 15 minutes. The mixture is then cooled to 0° C. Propargyl benzenesulfonate (1641.5 g, 837 moles) is then pumped into the reactor at such a rate as to maintain a temperature of between 0 and 5° C. When the addition is complete the reactor contents are warmed to 20–30° C.

Toluene (2500 g) is added to the reactor. A five-liter vessel equipped with an inlet tube and a dry ice condenser employed as a distillation receiver. Toluene (1334 g) is added to the five-liter flask. The end of the inlet tube from the reactor is placed below the surface to the toluene in the five-liter received to facilitate the collection of the 1,4-pentadiyne. Distillation of the 1,4-pentadiyne-toluene mixture is carried out at 0.5 mm Hg. The distillation is complete when the reactor temperature reaches 70° C. The weight of the 1,4-pentadiyne-toluene solution collected is 2961 g. By GC the composition is 14.53 wt % 1,4-pentadiyne, representing an 80% yield.

EXAMPLE 2

Preparation of 1,1-dibutylstannacyclohexia-2,5-diene

A solution of 4.42 kg of dibutyltin dichloride dissolved in 3.5 kg of toluene is added to a 50 L reactor. 8.97 kg of additional toluene is then added. Polymethyhydrosiloxane (1.7 kg) is added, followed by 1.7 kg of silica gel. A solution of 1,4-Penatadiyne in toluene (8.878 kg total, 936.4 g of pentadiyne, 14.51 moles) is then added to the stirred mixture.

A solution of potassium fluoride (4.2 kg) in water (6.25 kg) is then slowly added to the reactor, keeping the temperature during the addition below 30° C. A solution of 119 g of 2,2-azobis(isobutyronitrile) dissolved in 2.4 kg toluene is then added all at once to the reactor. The entire mixture is then heated to 65° C. for four hours, at which time an aliquot is taken which showed that the reaction had been completed.

After cooling to room temperature, the reaction contents are pumped through a centrifuge equipped with a 1-micron filter bag. The aqueous layer of the filtrate is separated. The organic layer is dried with magnesium sulfate (1 kg) and filtered through a pad of Celite into a distillation apparatus. The toluene is stripped off under vacuum (7 mm, 21–51° C.), leaving a viscous (3.2 kg) yellow oil, which is slowly getting red upon storage. NMR analysis showed that the desired product is a major component in the oil.

EXAMPLE 3

Preparation of 1-chloroboracyclohexa-2,5-diene

Approximately 2.74 kg of a 1,1-dibutylstannacyclohexa-2,5-diene solution (containing polymeric tin compounds) is placed in a reactor and diluted with 3.6 Kg of dichloromethane. This is cooled to −45° C. and a 13.2 Kg of a 1M solution of boron trichloride in dichloromethane is slowly added over a period of 4 hours, keeping the temperature at −25° C. After the addition is complete, the contents are warmed to room temperature over a 2–3 hour period. NMR analysis showed the reaction to be complete.

At this point, 976 g of octane and 630 g of nonane are added to the reactor contents. All of the dichloromethane is then removed under vacuum (100 mm Hg, 36° C.). Once all of the dichloromethane is removed, the product in octane/nonane solvent is distilled (5 mm Hg, temp 25–75° C.) into a dry ice cooled condenser over a 5 hour period. Typically about 2.1 kg of distillate is collected, containing about 10% product as analyzed by NMR.

EXAMPLE 4

Preparation of 1-Methylboracyclohexa-2,5-diene

A solution of 1-chloroboracyclohexa-2,5-diene in octane/nonane (2.3 Kg, 13.7% by weight of starting material) is placed into a dry, argon purged reactor and cooled to −10° C. The weight ratio of octane to nonane is about 5 to 3. A 2 M solution of trimethylaluminum in heptane (592 g) is slowly added to the chilled, stirred reactor. The temperature is kept below −5° C. during the addition. Following this, 364 g of di(ethyleneglycol) dibutyl ether is slowly added, again keeping the temperature below −5° C. The reactor contents are warmed to room temperature at which point a sample is taken for NMR analysis to ensure complete conversion of the starting material.

A receiver is charged with 500 mL octane and cooled in a dry ice acetone bath. The product, along with the octane/nonane solvent is distilled into this (4.0–1.2 mm Hg, 20–60° C.). The distillation is deemed complete when less than 10% liquids remained in the reactor pot.

EXAMPLE 5

Preparation of sodium 1-methylboratabenzene

A dry, argon purged reactor containing a dry ice acetone condenser is charged with 46.0 g of sodium hydride (dry). Tetrahydrofuran (174 g) is then added and the slurry is stirred. The reactor is cooled to 0° C. and a solution of 1-Methylboracyclohexa-2,5-diene in octane/nonane solvent (2.11 Kg containing 9.85% by weight staring material) is added slowly, keeping the temperature below 5° C. Hydrogen gas evolved as the staring material solution is added over a period of 4–5 hours.

After all of the staring material had been added, the reaction is warmed to room temperature. The solids are allowed to settle and a sample of the liquid is taken for NMR analysis. The reaction is deemed complete when the starting material is not present in the supernatant liquid.

The liquid layer is then carefully transferred into a Schlenk filter apparatus and into a second receiver, being careful to minimize any solids (the product) from being transferred. The wet solids are washed with 500 mL of pentane and the supernatant liquid is again carefully removed as before. The remaining liquid in the reactor is then removed by vacuum distillation into a dry ice cooled receiver.

Diethyl ether (1 L) is then added to the solids in the reactor. The reactor is stirred at room temperature for ½ hour to dissolve the product in ether. The reaction is then allowed to settle, and the liquid layer (containing the product) is carefully transferred through the same Schlenk filter as above into a dry, argon purged receiver. The above ether extraction procedure is repeated two more times to ensure complete removal of the product from any excess sodium hydride solids in the reactor. An aliquot is taken and analyzed by NMR.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for forming a boratabenzene having formula X:

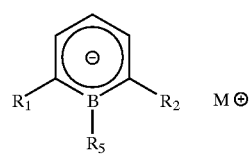

the method comprising:

1) reacting an alkynyl magnesium bromide having formula II:

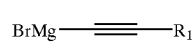

with a propargyl benzenesulfonate having formula III:

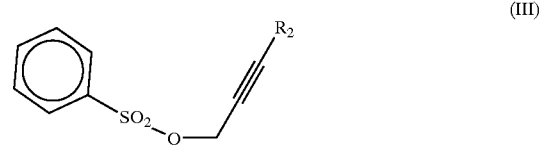

and with CuBr in a first chemically inert solvent to form a first solution containing a 1,4-pentadiyne having formula IV:

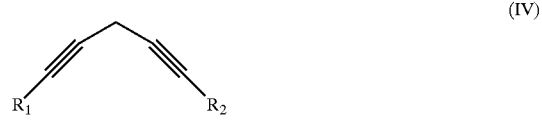

2) adding a second chemically inert solvent to the first solution to form a second solution of the 1,4-pentadiyne wherein the second solution has a greater volatility than the first solution;

3) distilling the second solution such that a third solution comprising the second solvent and the 1,4-pentadiyne is collected;

4) reacting the third solution with a tin dihydride having formula V:

to form a stannacyclohexa-2,5-diene having formula VI:

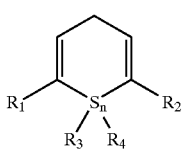

(VI)

5) reacting the stannacyclohexa-2,5-diene with a boron halide having formula VII:

BX$_3$ (VII)

to form a 1-haloboracyclohexa-2,5-diene having formula VIII:

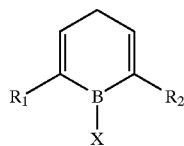

(VIII)

6) reacting the reacting the 1-haloboracyclohexa-2,5-diene with an alkylating agent to from a boracyclohexa-2,5-diene having formula IX:

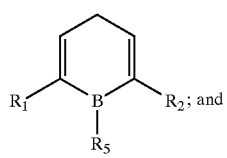

(IX)

7) reacting the boracyclohexa-2,5-diene with a strong base to form the boratabenzene: wherein,
R$_1$ is hydrogen, a C$_{1-10}$ alkyl group, a C$_{6-10}$ aryl group, or a C$_{7-15}$ aralkyl group;
R$_2$ is hydrogen, a C$_{1-10}$ alkyl group, a C$_{6-10}$ aryl group, or a C$_{7-15}$ aralkyl group;
R$_3$ is a C$_{1-10}$ alkyl group, a C$_{6-10}$ aryl group, or a C$_{7-15}$ aralkyl group;
R$_4$ is a C$_{1-10}$ alkyl group, a C$_{6-10}$ aryl group, or a C$_{7-15}$ aralkyl group;
R$_5$ is a C$_{1-10}$ alkyl group, a C$_{6-10}$ aryl group, or a C$_{7-15}$ aralkyl group;
X is a halogen; and
M$^+$ is a metal cation.

2. The method of claim 1 wherein the alkynyl magnesium bromide is formed by reacting an alkynyl magnesium chloride with lithium bromide.

3. The method of claim 1 wherein the alkynyl magnesium bromide is ethynylmagnesium bromide.

4. The method of claim 1 wherein the first chemically inert solvent is di(ethylene glycol) dibutyl ether.

5. The method of claim 1 wherein the second chemically inert solvent is toluene.

6. The method of claim 1, wherein the boron halide is boron trichloride.

7. The method of claim 1, wherein the alkylating agent is a trialkyl aluminum.

8. The method of claim 7, wherein the alkylating agent is trimethyl aluminum or triethyl aluminum.

9. The method of claim 7, wherein the alkylating agent is a dialkyl zinc.

10. The method of claim 8, wherein the alkylating agent is dimethyl zinc or diethyl zinc.

11. A method for forming a boratabenzene having formula X:

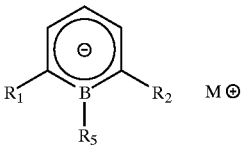

(X)

the method comprising:
1) reacting an alkynyl magnesium bromide having formula II:

(II)

with a propargyl benzenesulfonate having formula III:

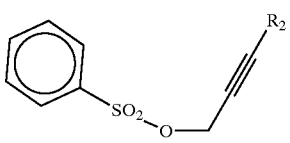

(III)

and with CuBr in a first chemically inert solvent to form a first solution containing a 1,4-pentadiyne having formula IV:

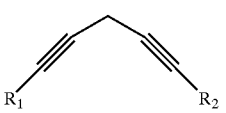

(IV)

2) adding a second chemically inert solvent to the first solution to form a second solution of the 1,4-pentadiyne wherein the second solution has a greater volatility than the first solution;

3) distilling the second solution such that a third solution comprising the second solvent and the 1,4-pentadiyne is collected;

4) reacting the third solution with a tin dihydride having the formula V:

(V)

to form a stannacyclohexa-2,5-diene having formula VI:

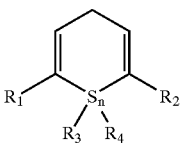

(VI)

5) reacting the stannacyclohexa-2,5-diene with

R₅BX₂ to form a boracyclohexa-2,5-diene having formula IX;

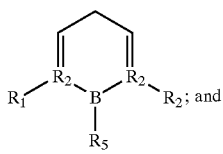
(IX)

6) reacting the boracyclohexa-2,5-diene with a strong base to form the boratabenzene; wherein
   R₁ is hydrogen, a $C_{1-10}$ alkyl group, a $C_{6-10}$ aryl group, or a $C_{7-15}$ aralkyl group;
   R₂ is hydrogen, a $C_{1-10}$ alkyl group, a $C_{6-10}$ aryl group, or a $C_{7-15}$ aralkyl group;
   R₃ is a $C_{1-10}$ alkyl group, a $C_{6-10}$ aryl group, or a $C_{7-15}$ aralkyl group;
   R₄ is a $C_{1-10}$ alkyl group, a $C_{6-10}$ aryl group, or a $C_{7-15}$ aralkyl group;
   R₅ is a $C_{1-10}$ alkyl group, a $C_{6-10}$ aryl group, or a $C_{7-15}$ aralkyl group;
   X is a halogen; and
   M⁺ is a metal cation.

12. The method of claim 11 wherein the alkynyl magnesium bromide is formed by reacting an alkynyl magnesium chloride with lithium bromide.

13. The method of claim 11 wherein the alkynyl magnesium bromide is ethynylmagnesium bromide.

14. The method of claim 11 wherein the first solvent is di(ethylene glycol) dibutyl ether.

15. The method of claim 11 wherein the second solvent is toluene.

16. A method for forming a boratabenzene having formula X:

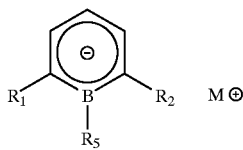
(X)

the method comprising:
1) reacting a 1,4-pentadiyne having formula IV:

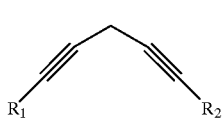
(IV)

with a solution comprising polymethylhydrosiloxane, potassium fluoride, a catalytic amount of 2,2-azobisisobutyronitrile, and a tin dichioride having formula XII:

(XII)

to form a stannacyclohexa-2,5-diene having formula VI:

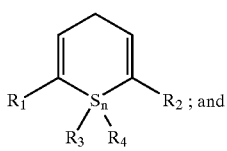
(VI)

2) reacting the stannacyclohexa-2,5-diene with a boron halide having the formula

BX₃ to form a 1-haloboracyclohexa-2,5-diene having formula VIII

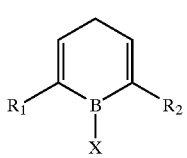
(VIII)

3) reacting the 1-haloboracyclohexa-2,5-diene with an alkylating agent to form a boracyclohexa-2,5-diene having formula IX:

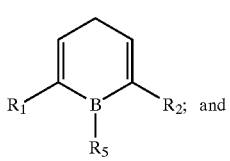
(IX)

4) reacting the boracyclohexa-2,5-diene with a strong base to form the boratabenzene; wherein
   R₁ is hydrogen, a $C_{1-10}$ alkyl group, a $C_{6-10}$ aryl group, or a $C_{7-15}$ aralkyl group;
   R₂ is hydrogen, a $C_{1-10}$ alkyl group, a $C_{6-10}$ aryl group, or a $C_{7-15}$ aralkyl group;
   R₃ is a $C_{1-10}$ alkyl group, a $C_{6-10}$ aryl group, or a $C_{7-15}$ aralkyl group;
   R₄ is a $C_{1-10}$ alkyl group, a $C_{6-10}$ aryl group, or a $C_{7-15}$ aralkyl group;
   R₅ is a $C_{1-10}$ alkyl group, a $C_{6-10}$ aryl group, or a $C_{7-15}$ aralkyl group;
   X is a halogen; and
   M⁺ is a metal cation.

17. The method of claim 16 wherein the boron halide is boron trichloride.

18. The method of claim 16 wherein the alkylating agent is a trialkyl aluminum.

19. The method of claim 18 wherein the alkylating agent is trimethyl aluminum.

20. The method of claim 16, wherein the alkylating agent is a dialkyl zinc.

21. The method of claim 20, wherein the alkylating agent is a dimethyl zinc.

* * * * *

UNITED STATES PATENT AND TRADEMARK OFFICE
CERTIFICATE OF CORRECTION

PATENT NO.    : 6,593,498 B2
DATED         : July 15, 2003
INVENTOR(S)   : Vladimir Dragan et al.

It is certified that error appears in the above-identified patent and that said Letters Patent is hereby corrected as shown below:

Column 3,
Lines 55-60, formula (V), delete "$S_n$" and insert -- Sn -- therefor.

Column 4,
Lines 1-8, formula (VI), delete "$S_n$" and insert -- Sn -- therefor.

Column 8,
Lines 60-65, formula (V), delete "$S_n$" and insert -- Sn -- therefor.

Column 9,
Lines 1-8, formula (VI), delete "$S_n$" and insert -- Sn -- therefor.

Column 10,
Lines 50-55, formula (V), delete "$S_n$" and insert -- Sn -- therefor.
Lines 60-65, formula (VI), delete "$S_n$" and insert -- Sn -- therefor.

Column 11,
Lines 60-65, formula (XII), delete "$S_n$" and insert -- Sn -- therefor.

Column 12,
Lines 1-8, formula (VI), delete "$S_n$" and insert -- Sn -- therefor.

Signed and Sealed this

Third Day of February, 2004

JON W. DUDAS
*Acting Director of the United States Patent and Trademark Office*